(12) United States Patent
Korir-Morrison et al.

(10) Patent No.: US 9,226,502 B2
(45) Date of Patent: Jan. 5, 2016

(54) FIBROUS WEB COMPRISING A CATIONIC POLYMER FOR CAPTURING MICROORGANISMS

(71) Applicant: Kimberly-Clark Worldwide, Inc., Neenah, WI (US)

(72) Inventors: Cindy Korir-Morrison, Smyrna, GA (US); Jonathan Hofmekler, Scottdale, GA (US); Cesar Z. Morales, Athens, GA (US); David William Koenig, Menasha, WI (US); Bao Trong Do, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 102 days.

(21) Appl. No.: 14/230,783

(22) Filed: Mar. 31, 2014

(65) Prior Publication Data

US 2015/0272117 A1    Oct. 1, 2015

(51) Int. Cl.
*B01J 20/26* (2006.01)
*A01N 37/46* (2006.01)
*A01N 25/34* (2006.01)

(52) U.S. Cl.
CPC ............... *A01N 37/46* (2013.01); *A01N 25/34* (2013.01)

(58) Field of Classification Search
CPC ........................................................ B01J 20/26
USPC ........................................................ 502/402
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,494,821 A | 2/1970 | Evans | |
| 3,502,763 A | 3/1970 | Hartman | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,041,203 A | 8/1977 | Brock et al. | |
| 4,100,324 A | 7/1978 | Anderson et al. | |
| 4,144,370 A | 3/1979 | Boulton | |
| 4,340,563 A | 7/1982 | Appel et al. | |
| 4,374,888 A | 2/1983 | Bornslaeger | |
| 4,708,870 A | 11/1987 | Pardini | |
| 5,057,361 A | 10/1991 | Sayovitz et al. | |
| 5,169,706 A | 12/1992 | Collier et al. | |
| 5,240,764 A | 8/1993 | Haid et al. | |
| 5,284,703 A | 2/1994 | Everhart et al. | |
| 5,350,624 A | 9/1994 | Georger et al. | |
| 5,389,202 A | 2/1995 | Everhart et al. | |
| 5,597,647 A | 1/1997 | Powers | |
| 5,688,157 A | 11/1997 | Bradley et al. | |
| 5,785,179 A | 7/1998 | Buczwinski et al. | |
| 5,883,026 A | 3/1999 | Reader et al. | |
| 5,888,754 A | 3/1999 | Pandian et al. | |
| 5,964,351 A | 10/1999 | Zander | |
| 6,030,331 A | 2/2000 | Zander | |
| 6,158,614 A | 12/2000 | Haines et al. | |
| 6,231,719 B1 | 5/2001 | Garvey et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,315,864 B2 | 11/2001 | Anderson et al. | |
| 6,936,554 B1 | 8/2005 | Singer et al. | |
| 7,939,601 B1 | 5/2011 | Bergeron et al. | |
| 8,709,466 B2 | 4/2014 | Coady et al. | |
| 2001/0040136 A1 | 11/2001 | Wei et al. | |
| 2002/0122939 A1 | 9/2002 | Wei et al. | |
| 2004/0000313 A1 | 1/2004 | Gaynor et al. | |
| 2004/0009141 A1 | 1/2004 | Koenig et al. | |
| 2004/0030080 A1 | 2/2004 | Chang et al. | |
| 2005/0130253 A1 | 6/2005 | Lye et al. | |
| 2005/0137540 A1 | 6/2005 | Villanueva et al. | |
| 2006/0163149 A1 | 7/2006 | Wadstrom et al. | |
| 2007/0141130 A1 | 6/2007 | Villanueva et al. | |
| 2007/0141934 A1 | 6/2007 | Sayre et al. | |
| 2007/0142262 A1 | 6/2007 | Sayre et al. | |
| 2008/0147029 A1 | 6/2008 | Pate et al. | |
| 2009/0155327 A1 | 6/2009 | Martin et al. | |
| 2010/0136072 A1 | 6/2010 | Haldar et al. | |
| 2011/0182959 A1 | 7/2011 | Cahill et al. | |
| 2012/0164206 A1 | 6/2012 | Soerens et al. | |
| 2012/0251608 A1 | 10/2012 | Coady et al. | |
| 2014/0034076 A1 | 2/2014 | Bergeron et al. | |

FOREIGN PATENT DOCUMENTS

| | | |
|---|---|---|
| CN | 1147575 | 4/1997 |
| CN | 101716359 | 6/2010 |
| CN | 102061614 | 5/2011 |
| WO | WO 2004/062703 | 7/2004 |

OTHER PUBLICATIONS

International Search Report and Written Opinion for PCT/IB2015/051962, Mailing Date of May 29, 2015.
Thermo Scientific Pierce LAL Chromogenic Endotoxin Quantitation Kit Instructions.

*Primary Examiner* — Edward Johnson
(74) *Attorney, Agent, or Firm* — Dority & Manning, P.A.

(57) ABSTRACT

A fibrous web that includes a cationic polymer that contains a cationic monomer comprising a cationic functional group having an affinity for the negatively charged cell walls of bacteria and a hydrophobic monomer comprising a hydrophobic functional group is provided. The molar ratio of the cationic monomer to the hydrophobic monomer is greater than about 1:1. The affinity of the cationic polymer for the bacteria allows the web to capture bacteria, thereby removing them from a surface or liquid, without the use of harsh chemicals, and also inhibiting their spread to other surfaces and liquids that may contact the web.

30 Claims, No Drawings

FIBROUS WEB COMPRISING A CATIONIC POLYMER FOR CAPTURING MICROORGANISMS

BACKGROUND OF THE INVENTION

The presence of various microorganisms such as bacteria, viruses, and fungi can put the population at risk for developing numerous illnesses and diseases. For instance, these microorganisms can be present on surfaces in hospitals, nursing homes, schools, restaurants, grocery stores, kitchens, bathrooms, gyms, etc. as well as in liquids such as drinking water. One approach for killing and/or removing these microorganisms is by using solutions containing detergents, biocides, antibiotics, or other chemicals. These solutions may also be impregnated into fibrous webs, such as wipes and nonwovens, for delivery to a contaminated surface or for filtration. However, although these substances can be successful in killing or removing the microorganisms, exposure to these chemicals can be harmful. Further, increased use can lead to the microorganisms having increased resistance to such chemicals. Additionally, over time, the use of such chemicals can corrode or damage the surfaces to which they are applied.

As concerns grow about allergic or toxicological reactions to chemicals and about the increasing resistance of bacteria to common chemicals and treatments, it has become more desirous to avoid harsh chemicals while still providing a fibrous web for removing microorganisms. Thus, to alleviate the aforementioned problems, another approach has been to attempt to remove the microorganisms without the use of chemicals, such as by utilizing the electrostatic interactions of the negatively charged bacteria. However, webs for capturing and trapping negatively charged bacteria are generally limited to the application of metal cation solutions such as aluminum cations to the surface of a web. First of all, these methods only utilize the cationic functionalities to interact with the negatively charged bacteria. Secondly, the metal cations are capable of leaching from the web and contaminating the surface and/or liquid that is in contact with the web.

In light of the above, a need exists for a technique for capturing and retaining microorganisms, such as bacteria, without the use of harsh chemicals.

SUMMARY OF THE INVENTION

In accordance with one embodiment of the present invention, a fibrous web for use in removing bacteria is disclosed wherein the web comprises a cationic polymer. The cationic polymer has an affinity for the negatively charged cell walls of bacteria. The cationic polymer comprises a cationic monomer and a hydrophobic monomer. The molar ratio of the cationic monomer to the hydrophobic monomer is greater than about 1:1.

In accordance with another embodiment of the present invention, a method for removing bacteria from a surface or a liquid is disclosed. The method comprises contacting the surface or the liquid with a fibrous web comprising a cationic polymer. The cationic polymer has an affinity for the negatively charged cell walls of bacteria. The cationic polymer comprises a cationic monomer and a hydrophobic monomer. The molar ratio of the cationic monomer to the hydrophobic monomer is greater than about 1:1.

Other features and aspects of the present invention are set forth in greater detail below.

DETAILED DESCRIPTION OF REPRESENTATIVE EMBODIMENTS

Definitions

It is to be understood that the terminology used herein is for the purpose of describing particular embodiments only and is not intended to limit the scope of the present invention.

"Alkyl" refers to monovalent saturated aliphatic hydrocarbyl groups having from 1 to 10 carbon atoms and, in some embodiments, from 1 to 5 carbon atoms. "$C_{x-y}$ alkyl" refers to alkyl groups having from x to y carbon atoms. This term includes, by way of example, linear and branched hydrocarbyl groups such as methyl($CH_3$), ethyl ($CH_3CH_2$), n-propyl ($CH_3CH_2CH_2$), isopropyl (($CH_3)_2CH$), n-butyl ($CH_3CH_2CH2CH_2$), isobutyl (($CH_3)_2CHCH_2$), sec-butyl (($CH_3)(CH_3CH_2)CH$), t-butyl (($CH_3)_3C$), n-pentyl ($CH_3CH_2CH_2CH_2CH_2$), and neopentyl (($CH_3)_3CCH_2$).

"Alkenyl" refers to a linear or branched hydrocarbyl group having from 2 to carbon atoms and in some embodiments from 2 to 6 carbon atoms or 2 to 5 carbon atoms and having at least 1 site of vinyl unsaturation ($>C=C<$). For example, ($C_x$-$C_y$) alkenyl refers to alkenyl groups having from x to y carbon atoms and is meant to include for example, ethenyl, propenyl, 1,3-butadienyl, and so forth.

"Aryl" refers to an aromatic group of from 3 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" applies when the point of attachment is at an aromatic carbon atom (e.g., 5,6,7,8 tetrahydronaphthalene-2-yl is an aryl group as its point of attachment is at the 2-position of the aromatic phenyl ring).

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benz-imidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N oxide (N→O), sulfinyl, or sulfonyl moieties. Examples of heteroaryl groups include, but are not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. decahydroquinolin-6-yl). In some embodiments, the nitrogen and/or sulfur atom(s) of the heterocyclic group are optionally oxidized to provide for the N oxide, sulfinyl, sulfonyl moieties. Examples of heterocyclyl groups include, but are not limited to, azetidinyl, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, thiomorpholinyl, imidazolidinyl, and pyrrolidinyl.

It should be understood that the aforementioned definitions encompass unsubstituted groups, as well as groups substituted with one or more other functional groups as is known in the art. For example, an aryl, heteroaryl, or heterocyclyl group may be substituted with from 1 to 8, in some embodiments from 1 to 5, in some embodiments from 1 to 3, and in some embodiments, from 1 to 2 substituents selected from alkyl, alkenyl, alkynyl, alkoxy, acyl, acylamino, acyloxy, amino, quaternary amino, amide, imino, amidino, aminocarbonylamino, amidinocarbonylamino, aminothiocarbonyl, aminocarbonylamino, aminothiocarbonylamino, aminocarbonyloxy, aminosulfonyl, aminosulfonyloxy, aminosulfonylamino, aryl, aryloxy, arylthio, azido, carboxyl, carboxyl ester, (carboxyl ester)amino, (carboxyl ester)oxy, cyano, cycloalkyl, cycloalkyloxy, cycloalkylthio, guanidino, halo, haloalkyl, haloalkoxy, hydroxy, hydroxyamino, alkoxyamino, hydrazino, heteroaryl, heteroaryloxy, heteroarylthio, heterocyclyl, heterocyclyloxy, heterocyclylthio, nitro, oxo, thione, phosphate, phosphonate, phosphinate, phosphonamidate, phosphorodiamidate, phosphoramidate monoester, cyclic phosphoramidate, cyclic phosphorodiamidate, phosphoramidate diester, sulfate, sulfonate, sulfonyl, substituted sulfonyl, sulfonyloxy, thioacyl, thiocyanate, thiol, alkylthio, etc., as well as combinations of such substituents.

DETAILED DESCRIPTION

It is to be understood by one of ordinary skill in the art that the present discussion is a description of exemplary embodiments only, and is not intended as limiting the broader aspects of the present invention.

Generally speaking, the present invention is directed to a fibrous web containing a plurality of fibers wherein the web also includes a cationic polymer. The cationic polymer is synthesized from a cationic monomer containing a cationic functional group that has an affinity for the negatively charged cell walls of microorganisms, such as bacteria. The ability of the polymer to attract and retain these microorganisms may be further enhanced by also incorporating a hydrophobic monomer. For instance, the hydrophobic functional groups present within the monomer may interact with the hydrophobic groups that are present in the cell walls of these microorganisms.

Therefore, utilizing both cationic and hydrophobic functional groups increases the interactions between the polymer and microorganisms which in turn enhances the ability of the polymer to capture and retain the microorganisms. Even further, when the polymer is applied to or incorporated within a fibrous web, the functional groups may also be capable of interacting, such as chemically, electrostatically, or physically, with the fibers of the fibrous web thereby immobilizing the polymer onto or within the web. For instance, the cationic functional groups may interact with functional groups, such as hydroxyl groups, on the fibers, such as cellulose fibers, within a fibrous web. In addition, the hydrophobic functional groups and polymer backbone may interact the other polymeric based materials and synthetic polymers, if any, incorporated within the web. As such, the polymer can become integral and become embedded into the web thereby inhibiting removal or transfer to another liquid, surface, or surrounding environment.

Furthermore, the present inventors have also discovered that these interactions can be optimized when utilizing the cationic monomer and the hydrophobic monomer in a specific ratio. For instance, the cationic polymer has a net positive charge wherein the molar ratio of the cationic monomer to the hydrophobic monomer is about 1:1 or more, and in another embodiment about 1.5:1 or more, and in a particular embodiment about 2:1 or more to about 15:1 or less, and in another embodiment about 10:1 or less, and in a particular embodiment about 5:1 or less such as at about 3:1. The present inventors have discovered that such molar ratio provides a cationic polymer that is capable of effectively interacting with bacteria while also remaining immobilized due to the interactions with the fibers of the fibrous web.

Gram positive bacteria, for example, contain teichoic acids that give the cell wall an overall negative charge due to the presence of phosphodiester bonds between teichoic acid monomers. Gram negative bacteria, on the other hand, contain highly charged lipopolysaccharides that may confer an overall negative charge to the cell wall. Regardless, the present inventors have discovered that utilizing a cationic polymer having cationic functional groups and hydrophobic functional groups in a specified ratio optimally enhances the ability of the polymer and web to capture and retain certain microorganisms, such as bacteria, thereby removing them from a surface or liquid and also inhibiting their spread. Of particular advantage, the polymer may help protect against the spread or infection of pathogens without the use of chemicals, such as antiseptics or antibiotics.

Various embodiments of the present invention will now be described in more detail below.

I. Cationic Polymer

The cationic polymer is employed in the present invention for interacting with the negatively charged well calls of microorganisms. These interactions allow the polymer to attract and retain negatively charged matter, such as molecules, particles, microbes, cells, fungi, anions, bacteria, other microorganisms, pathogens, and the like, through the application of physical means and Coulombic attraction, without the use of harsh chemicals such as some antimicrobials. As such, the cationic polymer prevents the transfer of bacteria through a fibrous web and prevents the spread of bacteria among surfaces and liquids that may contact the fibrous web.

The cationic polymer may have the general structure as identified in Formula I:

Formula I wherein:
A denotes a cationic monomer;
B denotes a hydrophobic monomer;
p is the number of units of monomer A and is greater than 1, such as from about 2 to about 2000, such as from about 2 to about 1000; and
q is the number of units of monomer B and is greater than 1, such as from about 2 to about 2000, such as from about 2 to about 1000.

As shown in Formula I, the cationic polymer contains a first monomer A and a second monomer B. Monomer A may be a cationic monomer and monomer B may be a hydrophobic monomer. Cationic monomer A may contain a cationic functional group while hydrophobic monomer B may contain a hydrophobic functional group.

In general, cationic functional groups are those that have a net positive charge. The presence of this charge is generally dictated by the pH of the environment in which the group is found. The groups are represented as charged functional groups generally at a physiological pH of 7.4. Without intending to be limited by theory, it is believed that the affinity of the cationic polymer for the negatively charged walls of microorganisms, such as bacteria, is generally due to the presence of these cationic functional groups that can electrostatically bind to the cell walls.

The ability of the polymer to attract and retain these microorganisms may be further enhanced by also incorporating a hydrophobic monomer having a hydrophobic functional group. In general, hydrophobic functional groups are groups without electronegative atoms thus preventing the ability to form a hydrogen bond with aqueous solvents. If hydrophobic, a molecule or part of a molecule will actively repel or exclude water. Without intending to be limited by theory, it is believed that the hydrophobic functional groups are also capable of interacting with the hydrophobic groups that are present in the cell walls of the microorganisms, such as bacteria.

Therefore, utilizing both cationic and hydrophobic functional groups increases the interactions between the polymer and microorganisms which in turn enhances the ability of the polymer to capture and retain the microorganisms. Even further, when the polymer is applied to or incorporated within a fibrous web, the functional groups may also be capable of interacting, such as chemically, electrostatically, or physically, with the fibers of the fibrous web thereby immobilizing the polymer onto or within the web. As such, the polymer can become integral and become embedded into the web thereby inhibiting removal or transfer to another liquid, surface, or surrounding environment.

For instance, the cationic functional groups may interact with functional groups, such as hydroxyl groups, on the fibers, such as cellulose fibers, within a fibrous web. In addition, the hydrophobic functional groups and polymer backbone may interact the other polymeric based materials and synthetic polymers, if any, incorporated within the web. Thus, the cationic polymer not only provides a surface of fixed functional groups for capturing and retaining bacteria but also provides functional groups for interacting with the fibers of the fibrous web.

Additionally, as shown in Formula I, p denotes the number of monomer units of monomer A present in the cationic polymer while q denotes the number of monomer units of monomer B present in the cationic polymer. For instance, p and q are greater than 1, such as from about 2 to about 2000, and in another embodiment from about 2 to about 1000.

According to one embodiment, the cationic monomer A is present in the polymer in an amount greater than the hydrophobic monomer B. For instance, the molar ratio (p:q) of the cationic monomer to the hydrophobic monomer is about 1:1 or more, and in another embodiment about 1.5:1 or more, and in a particular embodiment about 2:1 or more to about 15:1 or less, and in another embodiment about 10:1 or less, and in a particular embodiment about 5:1 or less. The present inventors have discovered that such ratios effectively enhance the ability of the cationic polymer to interact with the negatively charged cell walls of bacteria as well as the fibers of the fibrous web.

Additionally, the cationic polymer may have a molecular weight of about 10,000 g/mol or more, and in another embodiment about 25,000 g/mol or more to about 500,000 g/mol or less, and in another embodiment about 300,000 g/mol or less. In a particular embodiment the polymer is a water-soluble polymer having a molecular weight of from about 100,000 g/mol to about 200,000 g/mol. As used herein, the term "water-soluble" refers to materials which dissolve in water at 37° C. to give a true solution as opposed to materials which form a latex or suspension of undissolved particles.

The respective cationic monomer and hydrophobic monomers may be any monomers known in the art. For instance, in one embodiment, monomer may be an acrylamide monomer. As used herein, an acrylamide monomer may constitute an acrylamide, a methacrylamide, a derivative thereof, or a combination thereof. In another embodiment, the respective monomer may be an acrylate monomer or an acrylate ester monomer. As used herein, an acrylate monomer or acrylate ester monomer may be produced from acrylic acid or an acrylate, methacrylic acid or a methacrylate, a derivative thereof, or a combination thereof. Accordingly, in one embodiment, the polymer employed is a non-crosslinking polymer such that the rheology of the polymer system in solution is substantially retained and does not require further processing steps.

The monomers may be produced using any method known in the art. For instance, the monomers may be synthesized with a first constituent and a second constituent. In one embodiment, the first constituent may be an acrylate monomer produced from an acrylic acid or an acrylate, a methacrylic acid or a methacrylate, a derivative thereof, or a combination thereof. The second constituent may be a compound containing the cationic functional group or hydrophobic functional group. For instance, the carboxyl group of the first constituent may be reacted with the second constituent to form a carboxylic ester. In another embodiment, the carboxyl group of the first constituent may be reacted with an amine group of the second constituent to form an amide. Thus, any esterification reaction and/or amide synthesis known in the art may be utilized to produce the monomers for synthesis of the polymers. Additionally, the raw materials utilized to produce the monomers are commercially available from Sigma and whereby the monomers can be commercially synthesized by Lumigenix.

The second constituent may be any compound that is capable of providing the cationic functional group or hydrophobic functional group, as mentioned above, to the respective monomer. For instance, in one embodiment, the second constituent may be an amino acid, such as a natural amino acid. The amino acid may contain the desired cationic functional group or hydrophobic functional group. For instance, the second constituent may be arginine, lysine, histidine, alanine, valine, isoleucine, leucine, methionine, phenylalanine, tyrosine, and/or tryptophan. When it is desired to provide a cationic monomer having a cationic functional group, the second constituent may be arginine, lysine, histidine, or a combination thereof. In one particular embodiment, the second constituent for the cationic monomer is lysine. When it is desired to provide a hydrophobic monomer having a hydrophobic functional group, the second constituent may be alanine, valine, isoleucine, leucine, methionine, phenylalanine, tyrosine, tryptophan, or a combination thereof. In one particular embodiment, the second constituent for the hydrophobic monomer is phenylalanine.

Additionally, the cationic functional group and the hydrophobic functional group may be contained within their respective monomers such that they are capable of interacting with microorganisms, such as bacteria, and/or the fibers of a fibrous web. Accordingly, in one embodiment, the cationic functional group, hydrophobic functional group, or both may be present within the polymer backbone. In another embodiment, the cationic functional group, hydrophobic functional group, or both may be present as pendant functional groups attached to the backbone of the cationic polymer. In such embodiments, the pendant functional groups are extended or branched from the polymer backbone.

For instance, Formula II depicts a structure wherein the functional groups are present as pendant groups:

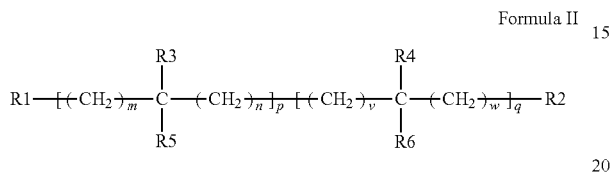

Formula II wherein:
R1 and R2 are each independently hydrogen, a $C_1$-$C_4$ alkyl group, or a $C_1$-$C_4$ alkenyl group;
R3 and R4 are each independently hydrogen, a hydroxyl group, a $C_1$-$C_4$ alkyl group, or a $C_1$-$C_4$ alkenyl group;
R5 is an organic substituent containing a cationic functional group;
R6 is an organic substituent containing a hydrophobic functional group;
p is the number of units of monomer A and is greater than 1, such as from about 2 to about 2000, such as from about 2 to about 1000;
q is the number of units of monomer B and is greater than 1, such as from about 2 to about 2000, such as from about 2 to about 1000; and
m, n, v, and w are each independently from 0 to 5, such as 0, 1, or 2.

As shown in Formula II, R1 and R2 are the terminal end groups of the cationic polymer. R1 and R2 may each independently be hydrogen, a $C_1$-$C_4$ alkyl group, or a $C_1$-$C_4$ alkenyl group. In one embodiment, R1, R2, or both are a $C_1$-$C_4$ alkyl group, such as a methyl, ethyl, propyl, or butyl group. In one embodiment, R1, R2, or both are a $C_1$-$C_2$ alkyl group. In a particular embodiment, R1, R2, or both are a methyl group.

As shown in Formula I, R3 and R4 are pendant groups that branch from the polymer backbone. R3 and R4 may each independently be hydrogen, a hydroxyl group, a $C_1$-$C_4$ alkyl group, or a $C_1$-$C_4$ alkenyl group. In one embodiment, R3, R4, or both are a $C_1$-$C_4$ alkyl group, such as a methyl, ethyl, propyl, or butyl group. In one embodiment, R3, R4, or both are a $C_1$-$C_2$ alkyl group. In a particular embodiment, R3, R4, or both are a methyl group.

Additionally, p and q are defined the same as with respect to the description of Formula I provided above. For instance, p and q are greater than 1, such as from about 2 to about 2000, and in another embodiment from about 2 to about 1000. Additionally, the molar ratio (p:q) of the cationic monomer to the hydrophobic monomer is about 1:1 or more, and in another embodiment about 1.5:1 or more, and in a particular embodiment about 2:1 or more to about 15:1 or less, and in another embodiment about 10:1 or less, and in a particular embodiment about 5:1 or less.

Additionally, R5 is an organic substituent containing a cationic functional group and R6 is an organic substituent containing a hydrophobic functional group. The formulae for R5 and R6 may have the general structures as identified in Formula III and Formula IV, respectively:

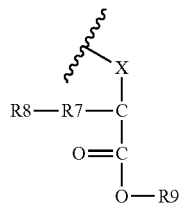

Formula III

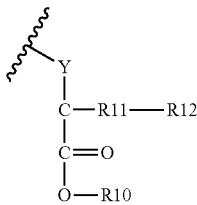

Formula IV wherein:
X and Y are each independently an amide (—C(O)NH— or —NHC(O)—) or a carboxylic ester (—C(O)O— or —OC(O)—);
R7 is a direct bond between the C and R8, a $C_1$-$C_5$ alkyl group, or a $C_1$-$C_5$ alkenyl group;
R8 is an amino group having the structure —N(R13)(R14), an ammonium group having the structure —N(R15)(R16)(R17), a N containing heteroaryl group, or a N containing heterocyclyl group;
R9 and R10 are each independently hydrogen, a $C_1$-$C_{10}$ alkyl group, or a $C_1$-$C_{10}$ alkenyl group;
R11 is a direct bond between the C and R12, a $C_1$-$C_5$ alkyl group, or a $C_1$-$C_5$ alkenyl group;
R12 is a $C_1$-$C_{20}$ alkyl group, a $C_2$-$C_{20}$ alkylene group, an aryl group, or a heteroaryl group;
R13 and R14 are each independently hydrogen, a $C_1$-$C_5$ alkyl group, a $C_1$-$C_5$ alkenyl group, or —C(NR18)N(R19)(R20);
R15, R16, and R17 are each independently hydrogen, a $C_1$-$C_5$ alkyl group, a $C_1$-$C_5$ alkenyl group, or —C(NR18)N(R19)(R20), wherein at least one of R15, R16, or R17 is hydrogen; and
R18, R19, and R20 are each independently hydrogen, a $C_1$-$C_5$ alkyl group, or a $C_1$-$C_5$ alkenyl group.

According to one embodiment, the cationic functional group may be contained within R8. For instance, R8 may be an amino group having the structure —N(R13)(R14), an ammonium group having the structure —N(R15)(R16)(R17), a N containing heteroaryl group, or a N containing heterocyclyl group. Accordingly, R8 may contain a N atom. In one embodiment, the N atom is protonated such that the cationic functional group is a protonated amine. As such, during protonation, the lone pair of electrons on the nitrogen atom is used to form a bond with hydrogen thus providing a protonated amine. Thus, the N atom will have four covalent bonds wherein one of the bonds is with a hydrogen atom.

When R8 is an amino group, the amino group may have the structure —N(R13)(R14). R13 and R14 are each independently hydrogen, a $C_1$-$C_5$ alkyl group, a $C_1$-$C_5$ alkenyl group, or —C(NR18)N(R19)(R20). In one embodiment, R13, R14, or both are hydrogen. In another embodiment, R13, R14, or both are a $C_1$-$C_5$ alkyl group, such as a $C_1$-$C_3$ alkyl group, such as a methyl group. In another embodiment, R13, R14, or both may be —C(NR18)N(R19)(R20). In such embodiments, when R13 or R14 is —C(NR18)N(R19)(R20), the other may be hydrogen. In these embodiments, R8 contains a guanidino group.

When R8 is an ammonium group, the ammonium group may have the structure —N(R15)(R16)(R17). R15, R16, and R17 are each independently hydrogen, a $C_1$-$C_5$ alkyl group, a $C_1$-$C_5$ alkenyl group, or —C(NR18)N(R19)(R20), wherein at least one of R15, R16, or R17 is hydrogen. In one embodiment, R15, R16, R17, or all three are hydrogen. In another embodiment, any one or two of R15, R16, or R17 is a $C_1$-$C_5$ alkyl group, such as a $C_1$-$C_3$ alkyl group, such as a methyl group. In another embodiment, any one of R15, R16, or R17 is —C(NR18)N(R19)(R20). In such embodiments, R8 contains a guanidino group.

When R8 contains a guanidino group, R18, R19, and R20 are each independently hydrogen, a $C_1$-$C_5$ alkyl group, or a $C_1$-$C_5$ alkenyl group. In one embodiment, R18, R19, R20, or all three are hydrogen. In one embodiment, the guanidino group may be protonated. In such embodiments, the nitrogen atom connected to the carbon atom via a double bond may further contain an additional hydrogen atom. In such embodiments, the guanidino group may have the structure —C(NR18R21)N(R19)(R20) wherein R21 is hydrogen.

When R8 contains a N containing heteroaryl group, the heteroaryl group may be any N containing heteroaryl group capable of providing a cationic functional group. For instance, the N containing heteroaryl group may be an imidazolyl group, a pyridyl group, a purinyl group, a pyrazolyl group, or a combination thereof. In one embodiment, the N containing heteroaryl group is an imidazolyl group.

As mentioned above, generally the N within R8 group is protonated to provide a protonated amine and thereby a cationic functional group. However, prior to protonation, the amine within R8 may be a primary amine, a secondary amine, or a tertiary amine. As used herein, a primary amine is referred to as an amine where only one of the hydrogens is replaced by an alkyl group or an aromatic group. A secondary amine is referred to as an amine where only two of the hydrogens are replaced by an alkyl group and/or an aromatic group. A tertiary amine is referred to as an amine wherein three of the hydrogens are replaced by an alkyl group and/or an aromatic group. In one particular embodiment, a primary amine is protonated to provide the protonated amine and the cationic functionality to the cationic monomer.

According to one embodiment, the hydrophobic functional group may be contained within R12. For instance, R12 may be a $C_1$-$C_{20}$ alkyl group, a $C_2$-$C_{20}$ alkylene group, an aryl group, or a heteroaryl group. In one embodiment, R12 is a $C_1$-$C_{20}$ alkyl group, such as a $C_5$-$C_{20}$ alkyl group.

In another embodiment, R12 is an aryl group or a heteroaryl group capable of providing a hydrophobic functional group. For instance, in one embodiment, the aryl group is a single aryl ring or a multiple fused aryl ring system, comprising two or more ring systems. In one embodiment, the aryl group is a single aryl ring such as a phenyl ring. In another embodiment, the aryl group is a fused aryl ring such as a naphthyl group or an anthryl group. In another embodiment, the aryl group is a heteroaryl group. For instance, the heteroaryl group may be a multiple fused heteroaryl ring system such as an indolyl group or an isoindolyl group. In one particular embodiment, the aryl group and/or heteroaryl group comprises a 6-membered carbon ring, such as a 6-membered aromatic carbon ring.

As shown in Formula III, R7 is connected to R8 which contains the cationic functional group. R7 is a direct bond between the C and R8, a $C_1$-$C_5$ alkyl group, or a $C_1$-$C_5$ alkenyl group. In one embodiment, R7 is a $C_1$-$C_5$ alkyl group, such as a $C_1$-$C_4$ alkyl group, such as a butyl group.

As shown in Formula IV, R11 is connected to R12 which contains the hydrophobic functional group. R11 is a direct bond between the C and R12, a $C_1$-$C_5$ alkyl group, or a $C_1$-$C_5$ alkenyl group. In one embodiment, R11 is a $C_1$-$C_5$ alkyl group, such as a $C_1$-$C_3$ alkyl group, such as a methyl group.

Referring to Formulae III and IV, R9 and R10, respectively, are each independently hydrogen, a $C_1$-$C_{10}$ alkyl group, or a $C_1$-$C_{10}$ alkenyl group. R9 and R10 may be the same or they may be different. In one embodiment, R9, R10, or both are hydrogen. In another embodiment, R9, R10, or both are a $C_1$-$C_{10}$ alkyl group, such as a $C_1$-$C_5$ alkyl group, such as a $C_1$-$C_3$ alkyl group, such as a methyl or ethyl group.

When R9 or R10 is hydrogen, the respective monomer is in a free acid form wherein the carboxylic acid is not reacted or esterified. However, when R9 or R10 contains an alkyl group or an alkylene group, the monomer may be considered esterified. As such, the carboxylic acid is reacted to form an ester. When in an ester form, the monomers may be esterified using any esterification reaction known in the art.

Without intending to be limited by theory, it is believed that the ester form of monomers further enhances the ability of the cationic polymer to interact with the negatively charged cell walls of bacteria. For instance, when the cationic polymer is present in a free acid form wherein the carboxylic acid of the amino acid is not esterified, the hydrogen of the hydroxyl moiety of the carboxylic acid may be released thereby forming a negatively charged carboxylate. Accordingly, the negatively charged carboxylate may not interact with the negatively charged cell walls of bacteria and may in fact result in repulsion of such bacteria. On the other hand, when the carboxylic acid is esterified with an alkyl group, the alkyl group may remain uncharged and thus may not negatively affect the interactions with the negatively charged cell walls of bacteria.

As shown in Formulae III and IV, X and Y, respectively are each independently an amide (—C(O)NH— or —NHC(O)—) or a carboxylic ester (—C(O)O— or —OC(O)—). When X or Y is an amide (—C(O)NH— or —NHC(O)—), the respective monomer may be referred to as an acrylamide monomer. As used herein, an acrylamide monomer may constitute an acrylamide, a methacrylamide, a derivative thereof, or a combination thereof. When X or Y is a carboxylic ester (—C(O)O— or —OC(O)—), the respective monomer may be referred to as an acrylate monomer or an acrylate ester monomer. As used herein, an acrylate monomer or acrylate ester monomer may be produced from acrylic acid or an acrylate, methacrylic acid or a methacrylate, a derivative thereof, or a combination thereof.

As discussed above, the cationic functional group and hydrophobic functional group are provided within the polymer so that they are capable of interacting with microorganisms, such as bacteria. As shown in Formula II, the functional groups are provided as pendant groups branching from the main chain. In one embodiment, the functional groups may be connected to the backbone of the cationic polymer by a spacer having a specific length. In general, the spacer arm length is the distance of the cationic functional group or the hydrophobic functional group from the polymer backbone. Accordingly, the spacer arm length is the length of the extension of the monomer due to the second constituent, such as the amino acid.

For instance, for the cationic monomer, the spacer arm length is the distance from R8 to X. The spacer length of the cationic functional group of the cationic monomer may be from about 3 Å to about 30 Å, in another embodiment from about 4 Å to about 20 Å, and in a particular embodiment from 5 Å to about 15 Å. Similarly, for the hydrophobic monomer, the spacer arm length is the distance from R12 to Y. The spacer length of the hydrophobic functional group of the hydrophobic monomer may be from about 2 Å to about 30 Å, in another embodiment from about 3 Å to about 20 Å, and in a particular embodiment from 4 Å to about 15

II. Fibrous Webs

In order to capture and retain microorganisms, such as bacteria, the cationic polymer may be applied to a fibrous web prior to use. Such fibrous webs may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The fibrous web may also be used to reduce microbial or viral populations by acting as a filter. The fibrous web may provide an increased surface area to facilitate contact of the cationic polymer with microorganisms. In addition, the fibrous web may also serve other purposes, such as providing water absorption, barrier properties, etc. The fibrous web may also eliminate microorganisms through frictional forces imparted to the surface.

The fibrous web may be provided in a variety of different forms, such as facial tissue, bath tissue, paper towels, napkins, absorbent articles, covers, wraps, and so forth. These webs may be formed from any of a variety of materials as is well known in the art. For example, the fibrous web may contain a plurality of absorbent fibers. The absorbent fibers may be formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable include those available from Kimberly-Clark Corporation under the trade designations "Longlac-19". Hardwood fibers, such as *eucalyptus*, maple, birch, aspen, and so forth, can also be used. In certain instances, *eucalyptus* fibers may be particularly desired to increase the softness of the web. *Eucalyptus* fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Savovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein in their entirety by reference thereto for all purposes. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein in its entirety by reference thereto for all purposes.

In addition to coform webs, hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 50% to about 80% by weight, such as in an amount of about 70% by weight. Commercially available hydroentangled composite webs as described above are commercially available from the Kimberly-Clark Corporation under the name HYDROKNIT. Hydraulic entangling is described in, for example, U.S. Pat. No. 5,389,202 to Everhart, which is incorporated herein in its entirety by reference thereto for all purposes.

In addition to the above, other fibrous webs may be used. For example, the cationic polymer may be incorporated into synthetic webs such as a meltblown web, a spunbond web, and laminates thereof.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Meltblown fibers are microfibers which may be continuous or discontinuous, are generally smaller than 10 microns in average diameter, and are generally tacky when deposited on a collecting surface.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo, et al., which are incorporated herein in their entirety by reference thereto for all purposes. Spunbond fibers are generally not tacky when they are deposited on a collecting surface. Spunbond fibers are generally continuous and have average diameters (from a sample of at least 10) larger than 7 microns, and more particularly, between about 10 and 40 microns.

Laminates containing meltblown webs and spunbond webs include, for instance, meltblown/spunbond laminates and spunbond/meltblown/spunbond (SMS) laminates. These laminates may be made by sequentially depositing layers onto a moving, forming surface. For instance, an SMS laminate may be made by depositing onto a moving, forming belt first a spunbond web, then a meltblown web, and then a spunbond web and bonding the layers. These layers may be bonded by thermal point bonding, adhesive bonding, hydroentanglement, needling, ultrasonic bonding, and the like. Such processes are disclosed, for example, in U.S. Pat. No. 4,041,203 to Brock et al., U.S. Pat. No. 5,169,706 to Collier, et al., U.S. Pat. No. 4,374,888 to Bornslaeger, U.S. Pat. No. 5,597,647 to Powers, U.S. Pat. No. 5,688,157 to Bradley, et al., U.S. Pat. No. 5,883,026 to Reader, et al., U.S. Pat. No. 6,936,554 to Singer, et al., and U.S. Patent Application Publication No. 2004/0000313 to Gaynor, et al.

Regardless of the materials or processes utilized to form the fibrous web, the basis weight of the web is typically from about 20 to about 200 grams per square meter ("gsm"), and in some embodiments, between about 35 to about 100 gsm. Lower basis weight products may be particularly well suited for light duty uses, while higher basis weight products may be better adapted for heavy duty or industrial uses.

In addition, the fibrous web may assume a variety of shapes, including but not limited to, generally circular, oval, square, rectangular, or irregularly shaped. In one embodiment, the web may be presented in the form of a wipe wherein the web is substantially saturated with a solution containing the cationic polymer. Each individual wipe may be arranged in a folded configuration and stacked one on top of the other to provide a stack of wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huana, et al.; and U.S. Pat. No. 6,273,359 to Newman, et al., which are incorporated herein in their entirety by reference thereto for all purposes.

III. Cationic Polymer Application and Incorporation

The cationic polymer may be applied to the fibrous web in the form of a solution. Although the exact quantity of the polymer employed may vary based on a variety of factors, including the presence of other additives, the suspected concentration of the microorganism, etc., it is typically present in the solution in an amount of from about 0.01 wt. % to about 20 wt. % and in some embodiments from about 0.1 wt. % to about 10 wt. %.

The polymer may be incorporated into the fibrous web during its formation or simply coated onto all or a portion of a surface of the fibrous web using known techniques, such as printing, dipping, spraying, melt extruding, coating (e.g., solvent coating, powder coating, brush coating, etc.), foaming, and so forth. In one embodiment, for example, the solution is applied to the fibrous web by dipping, spraying, or printing. If desired, the solution may be applied in a pattern that covers from about 5% to about 95%, in some embodiments from about 10% to about 90%, and in some embodiments, from about 20% to about 75% of a surface of the fibrous web. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

A variety of techniques may be used for applying the cationic polymer solution in the desired pattern. For instance, the solution may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of the substrate, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used.

Still another suitable contact printing technique that may be utilized is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the formulation(s) are to be printed. The formulation(s) are painted onto the screen, and transferred by rubbing the screen (which is in contact with the substrate) with a squeegee.

Ink-jet printing techniques may also be employed. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically.

In addition to the printing techniques mentioned above, any other suitable application technique may be used. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, etc. Such techniques are well known to those skilled in the art.

If desired, the fibrous web may be dried at a certain temperature to drive the solvents from the solution and form a concentrate. Such solution concentrates generally have a very high stability in storage. To use the fibrous web, water or an aqueous solution may simply be added. Drying may be accomplished using any known technique, such as an oven, drying rolls (e.g., through-air drying, Yankee dryer), etc. The temperature at which the fibrous web is dried generally depending on the time period over which it is dried, but is typically at least about 20° C., and in some embodiments, from about 30° C. to about 100° C. Drying may occur either before or after the solution is applied to the fibrous web. The solvent content (e.g., water content) of the resulting concentrate is thus typically less than about 5 wt. %, in some embodiments less than about 2 wt. %, and in some embodiments less about 1 wt. %.

The solids add-on level of the solution on the fibrous web is typically from about 5% to about 100%, in some embodiments from about 10% to about 80%, and in some embodiments from about 15% to about 70%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum functionality of the substrate, while higher add-on levels may provide optimum antimicrobial efficacy.

In addition to being employed as a concentrate, the solution may also be in the form of a liquid. This may be accomplished by simply not drying the solution after it is applied to the fibrous web. While the solids add-on level of such "wet wipes" generally remain within the ranges noted above, the total amount of the solution employed in such "wet wipes" (including any solvents) depends in part upon the type of web material utilized, the type of container used to store the wipes, the nature of the solution, and the desired end use of the wipes. Generally, however, each wet wipe contains from about 150 wt. % to about 600 wt. %, and desirably from about 300 wt. % to about 500 wt. % of the solution based on the dry weight of the web or wipe.

As a result of the present invention, it has been discovered that the cationic polymer may be employed to capture and retain microorganisms, such as bacteria (including cyanobacteria and Mycobacteria), protozoa, algae, and fungi (e.g., molds and yeast), viruses, prions, and other infectious particles. For example, the cationic polymer may be employed to capture and retain several medically significant bacteria groups, such as Gram negative rods (e.g., *Entereobacteria*); Gram negative curved rods (e.g., *Helicobacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g., *Ricckettsia* and *Chlamydia*); acid fast rods (e.g., *Myobacterium, Nocardia*, etc.); spirochetes (e.g., *Treponema, Borellia*, etc.); and mycoplasmas (i.e., bacteria that lack a cell wall). Particular species of bacteria that may be captured and/or retained with the cationic polymer of the present invention include *Escherichia coli* (Gram negative rod), *Klebsiella pneumoniae* (Gram negative rod), *Streptococcus* (Gram positive cocci), *Salmonella choleraesuis* (Gram negative rod), *Salmonella typhimurium* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

The present disclosure may be better understood by reference to the following examples.

EXAMPLES

The examples of the invention are given below by way of illustration and not by way of limitation. The following experiments were conducted in order to show some of the benefits and advantages of the present invention.

In the examples, two cationic polymers were prepared: Polymer 1 and Polymer 2. Polymer 1 is in a free acid form wherein the carboxyl group of the amino acid side group is presented as a carboxylic acid. Polymer 2 is in an ester form wherein the carboxyl group of the amino acid side group remains esterified, such as modified to provide a methyl group. Polymer 1 and Polymer 2 below were synthesized using Monomer A and Monomer B.

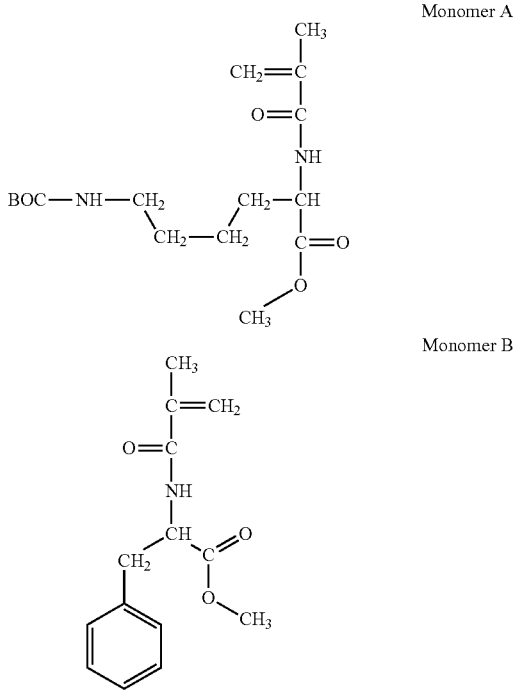

Monomer A

Monomer B

Polymer 1 was prepared by combining Monomer A and Monomer B with an initiator, azobisisobutyronitrile, and a solvent, isopropanol. The contents were purified under nitrogen for 0.5 hours. Polymerization was conducted at a temperature of 70° C. for approximately 24 hours under a nitrogen atmosphere and agitation. Then, to stop polymerization, 2 mL of tetrahydrofuran were added to the mixture. The polymer mixture was poured into 200 mL of n-hexane allowing the polymer to precipitate. The precipitate was separated via filtration under a reduced pressure. The precipitate was combined with 5 mL of dichloromethane and 2 mL of trifluoroacetic acid in a round bottom flask equipped with a liquid seal. The mixture was stirred at room temperature for 30 minutes. The solvent was removed via rotary evaporation under reduced pressure. The residue was dissolved in 5 mL of tetrahydrofuran. The mixture was combined with 200 mL of n-hexane allowing the polymer to precipitate. The precipitated product was filtered under reduced pressure. The final product was collected and dried under vacuum.

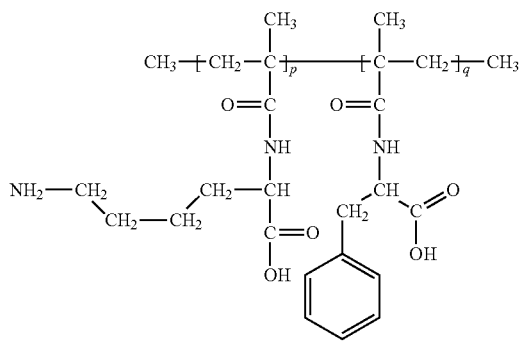

Polymer 1

Polymer 2 was prepared by combining Monomer A and Monomer B with an initiator, azobisisobutyronitrile, and a solvent, isopropanol. The contents were purified under nitrogen for 0.5 hours. Polymerization was conducted at a temperature of 70° C. for approximately 24 hours under a nitrogen atmosphere and agitation. Then, to stop polymerization, 2 mL of tetrahydrofuran were added to the mixture. The polymer mixture was poured into 200 mL of n-hexane allowing the polymer to precipitate. The precipitate was separated via filtration under a reduced pressure. The precipitate was combined with 20 mL of anhydrous ethyl acetate in a three-necked round bottom flask equipped with a liquid seal, thermometer, and an air duct. The flask was placed in an ice bath to keep the reaction temperature below 0° C. and dry hydrogen chloride gas was passed through the vessel for 0.5 hours. The precipitated product was filtered under reduced pressure. The final product was collected and dried under vacuum.

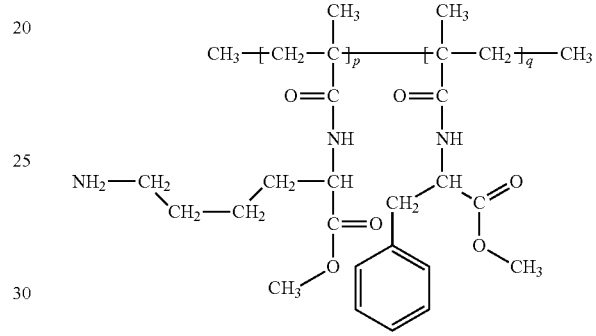

Polymer 2

The binding capacity of the polymers in solution with lipopolysaccharide (LPS) of *E. coli* and *Salmonella* was determined. Samples were prepared by mixing the lipopolysaccharide extract with a polymer suspension (5 g/mL) at a ratio of 1:1. A control sample was prepared by mixing lipopolysaccharide extract with phosphate buffered solution (PBS) at a ratio of 1:1. The samples were incubated at ambient temperature for 10 minutes and then centrifuged for 5 minutes at 9000 rpm. The supernatant was collected and analyzed using an LAL (Limulus Amebocyte Lysate) Chromogenic Assay kit from Thermo Scientific Pierce according to the manufacturer's instructions.

The amount of LPS present in the supernatant of the PBS control sample was compared to the supernatant of the samples containing Polymer A or Polymer B. In comparison to the control sample, the supernatant samples containing the cationic polymers contained at least 30% less LPS of *E. coli* and LPS of *Salmonella*.

TABLE 1

Reduction of LPS by LAL Chromogenic Assay.

| Polymer | % reduction of measured LPS from the control (mean ± SD, n = 3) | |
|---|---|---|
| (5 g/mL) | LPS of *E. coli* | LPS of *Salmonella* |
| 1 | 50.8 ± 6.0 | 37.4 ± 17.4 |
| 2 | 31.7 ± 15.0 | 44.1 ± 13.3 |

The antimicrobial effect of the polymers was determined. Samples were prepared by mixing 50 μL of a cell suspension (1:10000 dilution of overnight culture) with a 50 μL polymer suspension or a phosphate buffered solution control. The mixtures were incubated at room temperature for 5 minutes.

The suspensions were diluted 10-fold with 900 μL using maximum recovery diluents (MRD). The dilutions were plated onto a lysogeny broth (LB) agar plate using the spread plate method. The plates were incubated at 37° C. for up to 48 hours. The colony forming units were counted and analyzed based on the log reduction of the control.

TABLE 2

Log reduction of *E. coli* and *Salmonella typhimurium* colony forming units.

| Polymer | Log reduction against *E. coli* (mean ± SD, n = 3) | | Log reduction against *Salmonella* (mean ± SD, n = 3) |
|---|---|---|---|
| | 5 mg/ml | 10 mg/ml | 5 mg/ml |
| 1 | 0 ± 0.1 | 0.1 ± 0.1 | 0.1 ± 0.1 |
| 2 | Not tested | 0.1 ± 0.1 | Not tested |

The ability of a fibrous web containing the cationic polymers to capture and retain bacteria was determined. Test cultures were prepared by inoculating a single colony of bacteria into 10 mL of a lysogeny broth (LB) and incubating at 37° C. and 200 rpm overnight. The overnight culture may be washed by phosphate buffered solution twice, if necessary. Then a 1:10000 or 1:100 dilution in phosphate buffer with 5% (v/v) fetal bovine serum is prepared.

VIVA® (Kimberly-Clark) paper towels were cut into 1 cm$^2$ and placed into a 24 well microplate. Then, 20 μL of each polymer solution was added to a respective sample. The samples were allowed to dry at ambient temperature overnight. Then, 20 μL of each solution was added in a checkerboard pattern over the surface of the respective sample. The samples were inoculated at ambient temperature for 1 minute. The inoculated samples were placed in a separate 50 mL centrifuge tube with 5 mL phosphate buffered solution. The mixtures were agitated gently by swirling the tubes for 10 seconds. Dilutions were prepared and enumerated using the spread plate method. The mixtures were incubated at 37° C. for up to 48 hours. The colony forming units were counted and analyzed based on the log reduction of the control.

The following tables provide the colony-forming unit (CFU)/mL. The colony-forming unit is an estimate of viable bacteria. Additionally, the tables provide an indication of the amount of colonies released and trapped within the cationic polymers. Accordingly, the tables provide the ability of the webs containing the cationic polymers to reduce the amount of bacteria or microorganisms from a surface or liquid.

As shown, the web containing Polymer 1 was capable of trapping at least 90% while the web containing Polymer 2 was capable of trapping at least 85% of the LPS of *E. coli*. As shown, the web containing Polymer 1 was capable of trapping at least 90% of the LPS of *Salmonella*. As shown, the web containing Polymer 2 was capable of trapping at least 85% (with a sample concentration of 10 mg/mL) and at least 90% (with a sample concentration of 20 mg/mL) of the LPS of *Salmonella*.

TABLE 3

Trapping Effect of Polymers 1 and 2 in VIVA ® Towels Against *E. coli*

| Sample polymer concentration (mg/mL) | CFU/ml | Control CFU | Average Control CFU | CFU Released | % Released | CFU Trap | % Trap |
|---|---|---|---|---|---|---|---|
| Inoculum | 8.10E+05 | | | | | | |
| PBS Control 1 | 3.90E+03 | 1.93E+04 | 1.60E+04 | | | | |
| PBS Control 2 | 2.90E+03 | 1.46E+04 | | | | | |
| PBS Control 3 | 2.80E+03 | 1.41E+04 | | | | | |
| Untreated VIVA ® 1 | 3.20E+03 | | | 1.60E+04 | 100.10% | 0.00E+03 | −0.10% |
| Untreated VIVA ® 2 | 2.60E+03 | | | 1.30E+04 | 81.33% | 2.99E+03 | 18.67% |
| Untreated VIVA ® 3 | 2.30E+03 | | | 1.15E+04 | 71.95% | 4.49E+03 | 28.05% |
| Polymer 1-1 (20) | 2.70E+02 | | | 1.35E+03 | 8.45% | 1.46E+04 | 91.55% |
| Polymer 1-2 (20) | 2.10E+02 | | | 1.05E+03 | 6.57% | 1.49E+04 | 93.43% |
| Polymer 1-3 (20) | 1.30E+02 | | | 6.51E+02 | 4.07% | 1.53E+04 | 95.93% |
| Polymer 2-1 (20) | 4.70E+02 | | | 2.35E+03 | 14.70% | 1.36E+04 | 85.30% |
| Polymer 2-2 (20) | 4.00E+02 | | | 2.00E+03 | 12.51% | 1.40E+04 | 87.49% |
| Polymer 2-3 (20) | 4.50E+02 | | | 2.25E+03 | 14.08% | 1.37E+04 | 85.92% |

TABLE 4

Trapping Effect of Polymer 1 in VIVA ® Towels Against *Salmonella*

| Sample polymer concentration (mg/mL) | CFU/ml | Control CFU | Average Control CFU | CFU Released | % Released | CFU Trap | % Trap |
|---|---|---|---|---|---|---|---|
| Inoculum | 5.90E+05 | | | | | | |
| PBS Control 1 | 2.00E+03 | 1.02E+04 | 1.06E+04 | | | | |
| PBS Control 2 | 2.00E+03 | 1.01E+04 | | | | | |
| PBS Control 3 | 2.30E+03 | 1.14E+04 | | | | | |
| Untreated VIVA ® 1 | 1.10E+03 | | | 5.50E+03 | 52.05% | 5.07E+03 | 47.95% |
| Untreated VIVA ® 2 | 1.10E+03 | | | 5.50E+03 | 52.05% | 5.07E+03 | 47.95% |
| Untreated VIVA ® 3 | 1.00E+03 | | | 5.00E+03 | 47.32% | 5.57E+03 | 52.68% |
| Polymer 1-1 (20) | 4.50E+01 | | | 2.25E+02 | 2.13% | 1.03E+04 | 97.87% |
| Polymer 1-2 (20) | 1.80E+02 | | | 9.00E+02 | 8.52% | 9.67E+03 | 91.48% |
| Polymer 1-3 (20) | 5.00E+00 | | | 2.50E+01 | 0.24% | 1.05E+04 | 98.76% |

TABLE 5

Trapping Effect of Polymer 2 in VIVA ® Towels Against *Salmonella*

| Sample polymer concentration (mg/mL) | CFU/ml | Control | Average Control CFU | CFU Released | % Released | CFU Trap | % Trap |
|---|---|---|---|---|---|---|---|
| Inoculum | 4.10E+05 | | | | | | |
| PBS Control 1 | 2.10E+03 | 1.06E+04 | 9.27E+03 | | | | |
| PBS Control 2 | 1.70E+03 | 8.28E+03 | | | | | |
| PBS Control 3 | 1.80E+03 | 8.94E+03 | | | | | |
| Untreated VIVA ® 1 | 9.00E+02 | | | 4.50E+03 | 48.53% | 4.77E+03 | 51.47% |
| Untreated VIVA ® 2 | 1.10E+03 | | | 5.50E+03 | 59.31% | 3.77E+03 | 40.69% |
| Untreated VIVA ® 3 | 1.00E+03 | | | 5.00E+03 | 53.92% | 4.27E+03 | 46.08% |
| Polymer 2-1 (10) | 1.90E+02 | | | 9.50E+02 | 10.24% | 8.32E+03 | 89.78% |
| Polymer 2-2 (10) | 6.50E+01 | | | 3.25E+02 | 3.50% | 8.95E+03 | 96.50% |
| Polymer 2-3 (10) | 1.30E+02 | | | 6.50E+02 | 7.01% | 8.62E+03 | 92.99% |
| Polymer 2-1 (20) | 1.80E+02 | | | 9.00E+02 | 9.71% | 8.37E+03 | 90.29% |
| Polymer 2-2 (20) | 3.50E+01 | | | 1.75E+02 | 1.89% | 9.10E+03 | 98.11% |
| Polymer 2-3 (20) | 5.00E+01 | | | 2.50E+02 | 2.70% | 9.02E+03 | 97.30% |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A fibrous web for use in removing microorganisms, the web comprising a cationic polymer having an affinity for the negatively charged cell walls of bacteria, the cationic polymer comprising a cationic monomer and a hydrophobic monomer, wherein the molar ratio of the cationic monomer to the hydrophobic monomer is greater than about 1:1.

2. The fibrous web of claim 1, wherein the molar ratio of the cationic monomer to the hydrophobic monomer is from greater than about 1:1 to about 15:1.

3. The fibrous web of claim 1, wherein the cationic monomer comprises a protonated amine.

4. The fibrous web of claim 1, wherein the cationic monomer comprises an imidazolyl group, a pyridyl group, or a pyrazolyl group.

5. The fibrous web of claim 1, wherein the cationic monomer comprises an ammonium group.

6. The fibrous web of claim 1, wherein the hydrophobic monomer comprises a $C_5$-$C_{20}$ alkyl group, a $C_5$-$C_{20}$ alkylene group, an aryl group, or a heteroaryl group.

7. The fibrous web of claim 6, wherein the aryl group or heteroaryl group comprises a 6-membered aromatic carbon ring.

8. The fibrous web of claim 1, wherein the cationic monomer or hydrophobic monomer is an acrylamide monomer or a methacrylamide monomer.

9. The fibrous web of claim 1, wherein the cationic monomer or hydrophobic monomer is an acrylate ester monomer or a methacrylate ester monomer.

10. The fibrous web of claim 1, wherein a natural amino acid is used in the synthesis of the cationic polymer.

11. The fibrous web of claim 1, wherein an amino acid is used in the synthesis of the cationic monomer, the amino acid comprising arginine, lysine, histidine, or a combination thereof.

12. The fibrous web of claim 11, wherein the amino acid is lysine.

13. The fibrous web of claim 1, wherein an amino acid is used in the synthesis of the hydrophobic monomer, the amino acid comprising alanine, valine, isoleucine, leucine, methionine, phenylalanine, tyrosine, tryptophan, or a combination thereof.

14. The fibrous web of claim 13, wherein the amino acid is phenylalanine.

15. The fibrous web of claim 1, wherein the cationic monomer comprises a cationic functional group connected to a backbone of the cationic polymer by a first spacer, wherein the first spacer has a length of from about 3 Å to about 30 Å.

16. The fibrous web of claim 1, wherein the hydrophobic monomer comprises a hydrophobic functional group connected to a backbone of the cationic polymer by a second spacer, wherein the second spacer has a length of from about 2 Å to about 30 Å.

17. The fibrous web of claim 1, wherein the cationic polymer has the following structure:

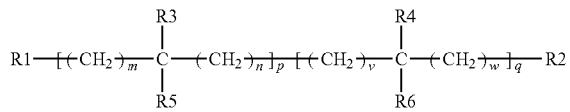

wherein:

R1 and R2 are each independently hydrogen, a $C_1$-$C_4$ alkyl group, or a $C_1$-$C_4$ alkenyl group;

R3 and R4 are each independently hydrogen, a hydroxyl group, a $C_1$-$C_4$ alkyl group, or a $C_1$-$C_4$ alkenyl group;

R5 comprises a cationic functional group;

R6 comprises a hydrophobic functional group;

p is greater than 1;

q is greater than 1;

m and n are independently from 0 to 5; and v and w are independently from 0 to 5.

18. The fibrous web of claim 1, wherein the cationic polymer comprises an organic substituent having the following structure:

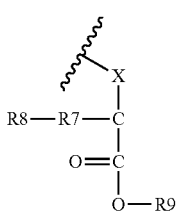

wherein:
- X is an amide (—C(O)NH— or —NHC(O)—) or a carboxylic ester (—C(O)O— or —OC(O)—);
- R7 is a direct bond between the C and R8, a $C_1$-$C_5$ alkyl group, or a $C_1$-$C_5$ alkenyl group;
- R8 is an amino group having the structure —N(R13)(R14), an ammonium group having the structure —N(R15)(R16)(R17), a N containing heteroaryl group, or a N containing heterocyclyl group;
- R9 is hydrogen, a $C_1$-$C_{10}$ alkyl group, or a $C_1$-$C_{10}$ alkenyl group;
- R13 and R14 are each independently hydrogen, a $C_1$-$C_5$ alkyl group, a $C_1$-$C_5$ alkenyl group, or —C(NR18)N(R19)(R20);
- R15, R16, and R17 are each independently hydrogen, a $C_1$-$C_5$ alkyl group, a $C_1$-$C_5$ alkenyl group, or —C(NR18)N(R19)(R20), wherein at least one of R15, R16, or R17 is hydrogen; and
- R18, R19, and R20 are each independently hydrogen, a $C_1$-$C_5$ alkyl group, or a $C_1$-$C_5$ alkenyl group.

19. The fibrous web of claim 18, wherein R8 is an amino group having the structure —N(R13)(R14).

20. The fibrous web of claim 19, wherein R13 and R14 are hydrogen.

21. The fibrous web of claim 18, wherein R8 is an ammonium group having the structure —N(R15)(R16)(R17), wherein R15, R16, and R17 are hydrogen.

22. The fibrous web of claim 18, wherein R9 is hydrogen or a $C_1$-$C_3$ alkyl group.

23. The fibrous web of claim 1, wherein the cationic polymer comprises an organic substituent having the following structure:

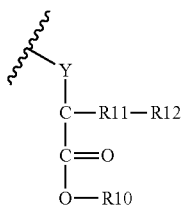

wherein:
- Y is an amide (—C(O)NH— or —NHC(O)—) or a carboxylic ester (—C(O)O— or —OC(O)—);
- R10 is hydrogen, a $C_1$-$C_{20}$ alkyl group, or a $C_1$-$C_{10}$ alkenyl group;
- R11 is a direct bond between the C and R12, a $C_1$-$C_5$ alkyl group, or a $C_1$-$C_5$ alkenyl group; and
- R12 is a $C_1$-$C_{20}$ alkyl group, a $C_2$-$C_{20}$ alkylene group, an aryl group, or a heteroaryl group.

24. The fibrous web of claim 23, wherein R12 is an aryl group.

25. The fibrous web of claim 23, wherein the aryl group is a phenyl group.

26. The fibrous web of claim 23, wherein R12 comprises a 6-membered aromatic carbon ring.

27. The fibrous web of claim 23, wherein R10 is hydrogen or a $C_1$-$C_3$ alkyl group.

28. The fibrous web of claim 1, wherein the web further comprises absorbent fibers.

29. The fibrous web of claim 1, wherein the web further comprises synthetic thermoplastic fibers.

30. The fibrous web of claim 1, wherein the web is a composite of absorbent fibers and synthetic thermoplastic fibers.

* * * * *